(12) United States Patent
Delessert et al.

(10) Patent No.: US 8,197,653 B2
(45) Date of Patent: Jun. 12, 2012

(54) ELECTROLYTE CARTRIDGE UNIT FOR AN ELECTROCHEMICAL SENSOR

(75) Inventors: Yannick Delessert, Onex (CH); Daniel Rosset, Veyrier (CH); Gérard Stehlé, Machilly (FR); James Hide, Grand-Lancy (CH); Serge Hediger, Lausanne (CH)

(73) Assignee: Hach Lange Sarl (Hach Lange GmbH), Vesenaz (CH)

( * ) Notice: Subject to any disclaimer, the term of this patent is extended or adjusted under 35 U.S.C. 154(b) by 852 days.

(21) Appl. No.: 12/269,492

(22) Filed: Nov. 12, 2008

(65) Prior Publication Data

US 2009/0120792 A1 May 14, 2009

(30) Foreign Application Priority Data

Nov. 14, 2007 (CH) ...................................... 1759/07

(51) Int. Cl.
*G01N 27/403* (2006.01)
(52) U.S. Cl. ......................... 204/432; 204/431; 205/781
(58) Field of Classification Search .................. 204/410, 204/411, 421–429, 431, 432; 205/781, 783.5–785, 205/787; 73/23.31, 23.32
See application file for complete search history.

(56) References Cited

U.S. PATENT DOCUMENTS

| | | | | |
|---|---|---|---|---|
| 3,410,778 A | * | 11/1968 | Krasberg | 204/414 |
| 4,466,878 A | * | 8/1984 | DiNitto et al. | 204/415 |
| 2005/0034987 A1 | * | 2/2005 | Zhou et al. | 204/426 |

OTHER PUBLICATIONS

Anthoni "The Dark Decay Assay" http://www.seafriends.org.nz/dda/manual.htm, pp. 1-7, May 2, 2006.*

* cited by examiner

*Primary Examiner* — Kaj K Olsen
*Assistant Examiner* — Susan D Leong
(74) *Attorney, Agent, or Firm* — Bacon & Thomas, PLLC

(57) ABSTRACT

Cartridge unit for an electrochemical sensor includes a cartridge (2) prefilled with electrolyte and having a first end closed by a selectively permeable membrane (7), and a second end (6) having a fastening device (11) arranged for fastening the cartridge to the electrochemical sensor (24). The cartridge unit further has a supporting member (3) to which the cartridge (2) is detachably fastened, and closing devices (4, 20) for closing the second end (6) of the cartridge (2). These closing devices (4, 20) are able to be opened by a user to allow the cartridge (2) to be fastened to the electrochemical sensor (24) and then to be detached from the supporting element (3).

11 Claims, 3 Drawing Sheets

ELECTROLYTE CARTRIDGE UNIT FOR AN ELECTROCHEMICAL SENSOR

FIELD OF THE INVENTION

The present invention relates to the field of electrochemical sensors. Such sensors are used to detect the presence and measure the amount of determined substances in a fluid sample. In particular, electrochemical sensors exist for measuring the partial pressure or concentration of a gas, such as oxygen, hydrogen or ozone, in a liquid or in a gas mixture.

BACKGROUND

Generally, an electrochemical sensor comprises polarized electrodes (cathode and anode), one of which protrudes at one end of the sensor where it rests against a membrane selectively permeable to the substance to be detected, that is, a membrane that will let pass said substance but will not, or will less readily, let pass the other substances of the fluid to be analyzed. The membrane closes a recess where the end of the sensor is accommodated, and which is filled with an electrolyte. An electrolyte film is inserted between said protruding electrode and the membrane. The other electrode is also in contact with the electrolyte. The outer surface of the membrane is in contact with the fluid sample to be analyzed. The substance to be detected diffuses across the membrane in response to a pressure difference between the two sides of the membrane, and participates in an electrochemical reaction that produces an electrical current between the electrodes. The intensity of this current is a function of the amount of said substance in the fluid.

Such electrochemical sensors require regular upkeep. The electrolyte and the membrane indeed deteriorate with time, and must thus be periodically replaced. While replacing the electrolyte the user must pay particular attention to avoid any contact between his/her skin and the electrolyte. The latter indeed is a caustic product. For this reason, the operation of electrolyte transfer from the supplier bottle to said sensor recess is delicate.

SUMMARY

The present invention aims at furnishing a cartridge unit for an electrochemical sensor that will notably lower the risks in terms of user health that are associated with electrolyte replacement.

To this end, a cartridge unit for an electrochemical sensor is proposed that comprises:
- a cartridge prefilled with electrolyte and comprising a first end closed by a selectively permeable membrane, a second end and means for fastening to the electrochemical sensor,
- a supporting member to which the cartridge is detachably fastened,
- means for closing the second end of the cartridge, these closing means being able to be opened by a user so as to allow the cartridge to be fastened to the electrochemical sensor and then to be detached from the supporting member.

The cartridge unit according to the invention thus allows a user to mount the cartridge onto the electrochemical sensor without transfer of electrolyte from a bottle into the cartridge. The supporting member helps mounting the cartridge onto the electrochemical sensor, and allows direct contact between the user and the cartridge to be avoided.

In a preferred embodiment, the supporting member is a case that entirely contains the cartridge. A lid may be provided to close the case.

Advantageously, the supporting member comprises a space for receiving excess electrolyte from the cartridge during fastening of the cartridge to the electrochemical sensor.

The cartridge unit can be arranged in such a way that fastening of the cartridge to the supporting member is achieved by applying a first clamping torque, and that fastening of the cartridge to the electrochemical sensor is achieved by applying a second clamping torque the value of which is necessarily substantially the same as that of the first clamping torque.

To this end, the cartridge unit may be arranged in such a way that:
- said means for fastening to the electrochemical sensor comprise a first thread,
- the cartridge comprises a second thread that cooperates with a corresponding thread of the supporting member, and
- the pitches of the first and second threads are reversed.

The first end of the cartridge may comprise a gasket retained by the membrane in a groove, this gasket being compressed by a surface of the supporting member.

The second end of the cartridge may comprise a gasket sitting in a groove and being compressed by the closing means.

Preferably, the supporting member comprises an elastic member exerting pressure upon the outer surface of the membrane. A member connected with said closing means, and resting against the inner surface of the membrane so as to counter the action of the elastic member, may also be provided in order to keep the membrane in a substantially undeformed state.

The present invention further relates to an assembly comprising a cartridge unit as defined hereinabove and an electrochemical sensor.

This assembly may comprise a protecting sleeve able to receive at least the cartridge, after it has been fastened to the electrochemical sensor, this protecting sleeve protecting a body of the cartridge from a sample to be analyzed.

Advantageously, the protecting sleeve comprises a projecting member for compressing said gasket that is retained in a groove by the membrane.

BRIEF DESCRIPTION OF THE DRAWINGS

Other characteristics and advantages of the present invention will become apparent upon reading the following detailed description provided while referring to the attached drawing where.

DETAILED DESCRIPTION OF EXEMPLARY EMBODIMENTS OF THE INVENTION

Figure 1:
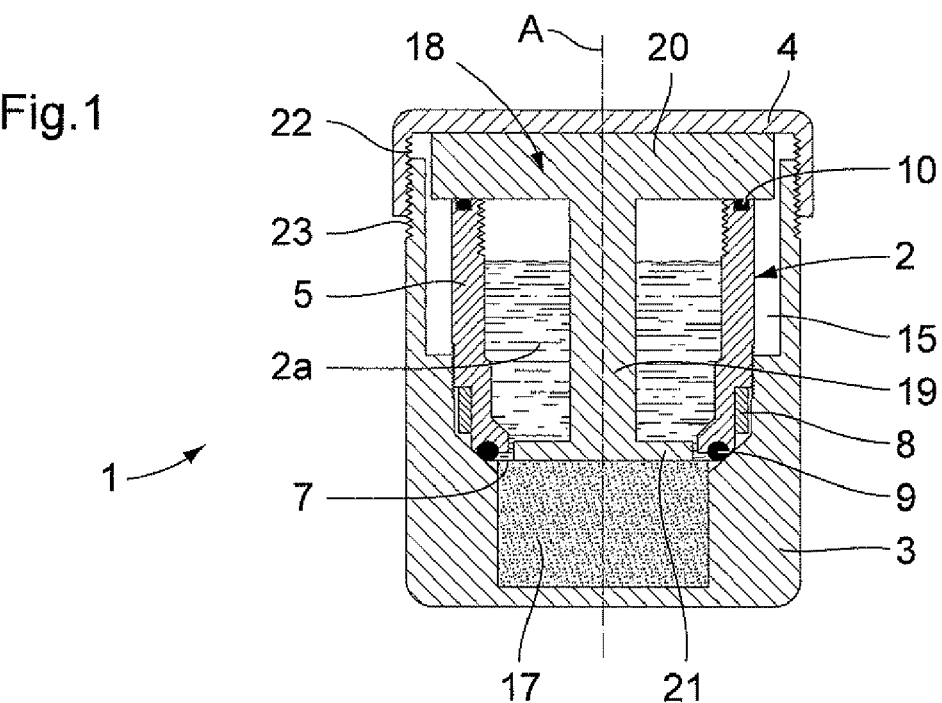
FIG. 1 is an axial sectioned view of a cartridge unit according to the invention.
Figure 2:
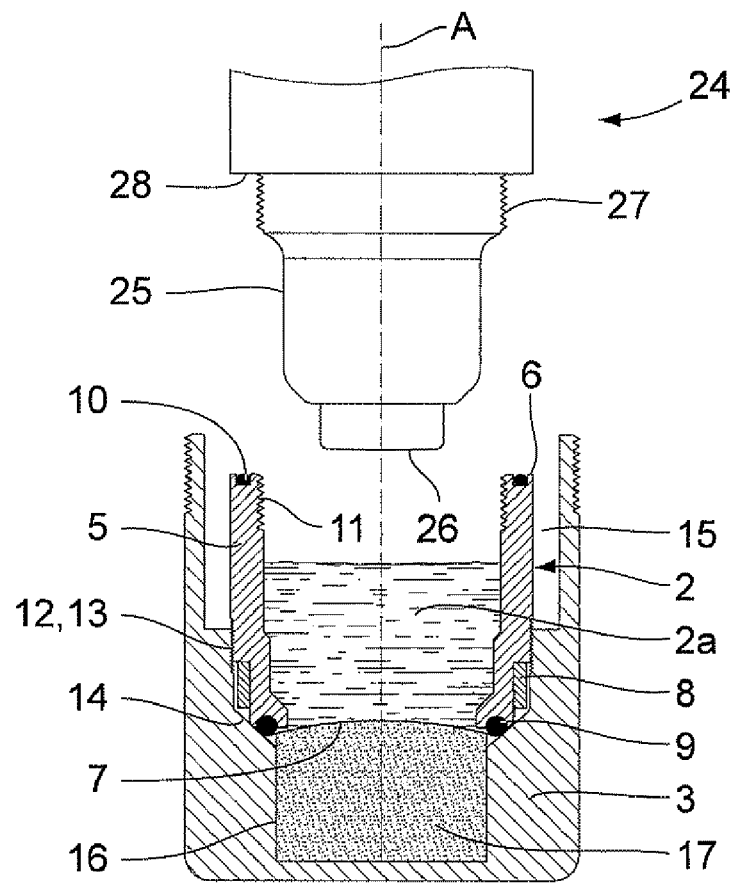
FIGS. 2 to 6 are axial sectioned views showing successive steps of mounting a cartridge contained in the cartridge unit of FIG. 1 to an electrochemical sensor.

Referring to FIGS. 1 and 2, a cartridge unit 1 according to the invention for an electrochemical sensor, comprises a cartridge 2 placed into a case 3 closed by a lid 4.

The cartridge 2 comprises a hollow cartridge body 5 of generally cylindrical or conical shape that is open at an axial end 6, as well as a membrane 7 closing the other axial end of cartridge body 5. The membrane 7 is selectively permeable to a substance, such as a gas, to be detected. A ring 8 forced over the periphery of cartridge body 5 fastens the membrane 7 to this cartridge body. The end of cartridge body 5 where membrane 7 is situated includes a groove in which a gasket 9 in the form of an O-ring is provided. The gasket 9 is held within the groove by membrane 7. Another gasket 10, of annular shape in the example shown, is arranged within a groove made in the open end 6 of cartridge body 5. A thread 11 is made in the inner surface of cartridge body 5 close to the open end 6. Another thread 12 is made in the outer surface of cartridge body 5 close to membrane 7. The thread pitches of threads 11 and 12 are reversed. Cartridge 2 is partly filled with a certain amount of electrolyte 2a.

Case 3 serves as a support, storage means, and mounting tool for cartridge 2. Case 3 includes a first recess into which cartridge 2 is screwed and which has the same axis as the common axis A of case 3 and cartridge 2. This recess is defined by a threaded cylindrical surface 13 cooperating with the outer thread 12 of cartridge 2, and a subsequent truncated conical surface 14 widening out toward the open end 6. Cartridge 2 is axially blocked in the direction of the bottom of case 3 by the truncated conical surface 14, against which gasket 9 rests and is compressed. The height of case 3 (i.e. its dimension in the direction of axis A) is sufficiently large for case 3 to reach beyond the open end 6 of the cartridge body 5 or, said otherwise, for the cartridge 2 to be entirely contained within case 3. An empty annular cylindrical space 15 is defined, axially between the open end 6 of cartridge body 5 and the threaded surface 13, and radially between cartridge 2 and case 3.

In addition, case 3 close to its bottom includes a second recess 16 that communicates with the first recess. The second recess 16 has a cylindrical or conical shape, and is filled with an elastic cushion 17, consisting of foam for example. This cushion 17 exerts pressure onto the outer surface of membrane 7, that is, the surface turned toward the outside of cartridge 2, in order to stretch the membrane 7, as shown in FIG. 2.

An insert 18 is placed inside case 3 and cartridge 2. Insert 18 comprises an elongated segment 19 along axis A terminating into end plates 20 and 21 at its two ends. The elongated segment 19 and end plates 20, 21 are rigidly connected to one another. Insert 18 may consist of a single piece, as in the example shown. End plate 21, smaller in size than end plate 20, rests against the inner surface of membrane 7, and opposes the force exerted by elastic cushion 17 in order to maintain membrane 7 in a substantially undeformed state (FIG. 1). End plate 20 closes cartridge 2 by plugging and resting against the open end 6 of cartridge body 5 and by compressing gasket 10.

Insert 18 is maintained in its axial position as shown in FIG. 1, against the action of elastic cushion 17, by virtue of the lid 4 pressing against the outer surface of end plate 20. Lid 4 is screwed to case 3 by cooperation between an inner thread 22 of lid 4 and a thread 23 made on the periphery of case 3.

By the compression of gaskets 9, 10 that is produced by the truncated conical surface 14 and by end plate 20, it is possible to preserve a high tightness of cartridge 2 preventing the electrolyte from escaping from cartridge 2. In addition, the absence of deformation of membrane 7 that is achieved by virtue of end plate 21 protects the membrane 7. Indeed, without insert 18 and its end plate 21, the constant action exerted by cushion 17 could make the deformation of membrane 7 permanent after a certain time.

One sees that the cartridge unit 1 according to the invention thus includes a cartridge 2 prefilled with electrolyte. Case 3, lid 4 and insert 18 yield an extended preservation of cartridge 2 without the risk of deterioration of membrane 7 or of escape of electrolyte 2a. Moreover, as will be apparent below, since cartridge 2 is prefilled by the manufacturer, the amount of electrolyte 2a in cartridge 2 may be defined for optimum functioning of the electrochemical sensor.

The electrochemical sensor onto which cartridge 2 is to be mounted is represented schematically and partially in FIGS. 2 to 6 where it is designated by the reference numeral 24. This sensor 24 comprises a head 25 having an end face 26 from which one or several electrodes project, namely a polarized measuring electrode, cathode or anode depending on the substance to be detected, and optionally a guard electrode surrounding the measuring electrode. In addition, sensor 24 includes a second polarized electrode, anode or cathode depending on the substance to be detected. These electrodes are known per se and are not represented in the figures. A piece of cellulose may be placed onto membrane 7 of cartridge 2 between the measuring electrode and the second polarized electrode, in order to block the migration of silver ions coming from the second polarized electrode, in a way known per se. A thread 27 is made in the periphery of head 25 of sensor 24. This thread 27 is intended to cooperate with the inner thread 11 of cartridge 2.

The way of fastening cartridge 2 to sensor 24 will now be described while referring to FIGS. 2 to 6.

Figure 3:
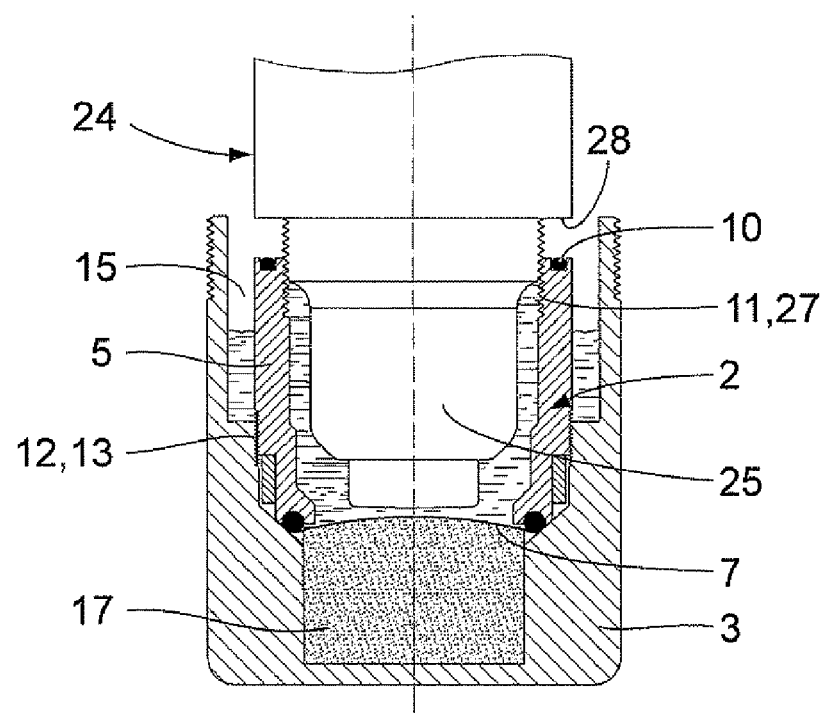
Figure 4:
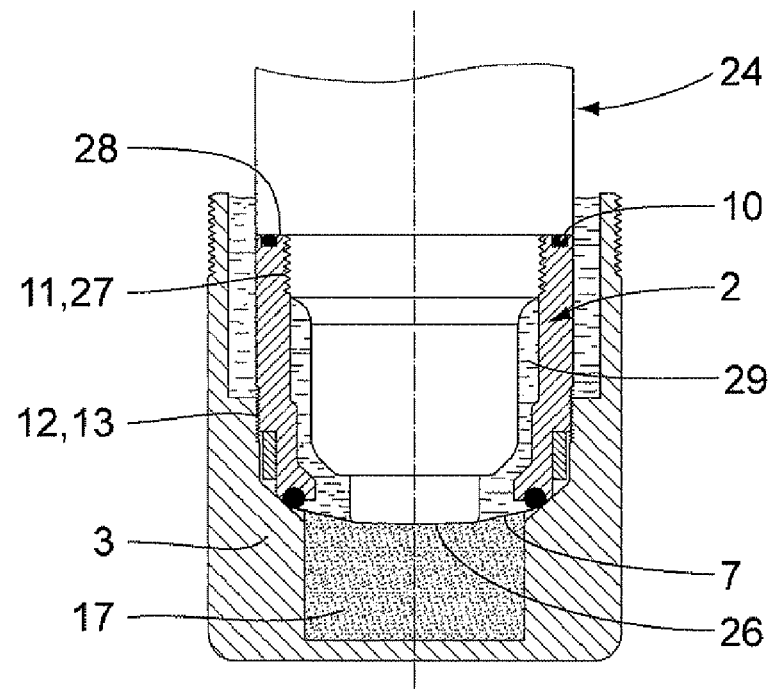

First of all, lid 4 and insert 18 are removed, so as to open case 3 and cartridge 2 (FIG. 2). Then, head 25 of the electrochemical sensor 24 is introduced into cartridge 2, and screwed into it by the cooperation of threads 11 and 27 (FIG. 3). While screwing, an excess of electrolyte is evacuated from cartridge 2 via the open end 6 and across threads 11, 27 so as to drop into the annular space 15 between the wall of case 3 and the cartridge 2. Channels (not shown) closed by a valve and communicating with space 15 may be provided across the wall of cartridge body 5 in order to facilitate evacuation of the excess electrolyte. Head 25 of the sensor is screwed into cartridge 2 down to the point where a shoulder 28 of the sensor abuts against the open end 6 of cartridge 2 while compressing gasket 10 (FIG. 4). At this point, cartridge 2 is tightly closed by sensor 24. In addition, the inner space 29 between sensor 24 and cartridge 2 is entirely filled with electrolyte, in other words, the inside of cartridge 2 no longer contains any air, which is an important condition for the good functioning of sensor 24. At this point, too, the end surface 26 of sensor 24 exerts pressure onto the inner surface of membrane 7, causing membrane 7 to be stretched by compression of the elastic cushion 17. Although not visible in FIG. 4, an electrolyte film is present between the electrode(s) of the end surface 26 of sensor 24 and the membrane 7. The pressure exerted by the elastic cushion 17 guarantees that membrane 7 is pressing against this or these electrodes (with the electrolyte film in between). The second polarized electrode of sensor 24 is in contact with the electrolyte as well.

Figure 5:
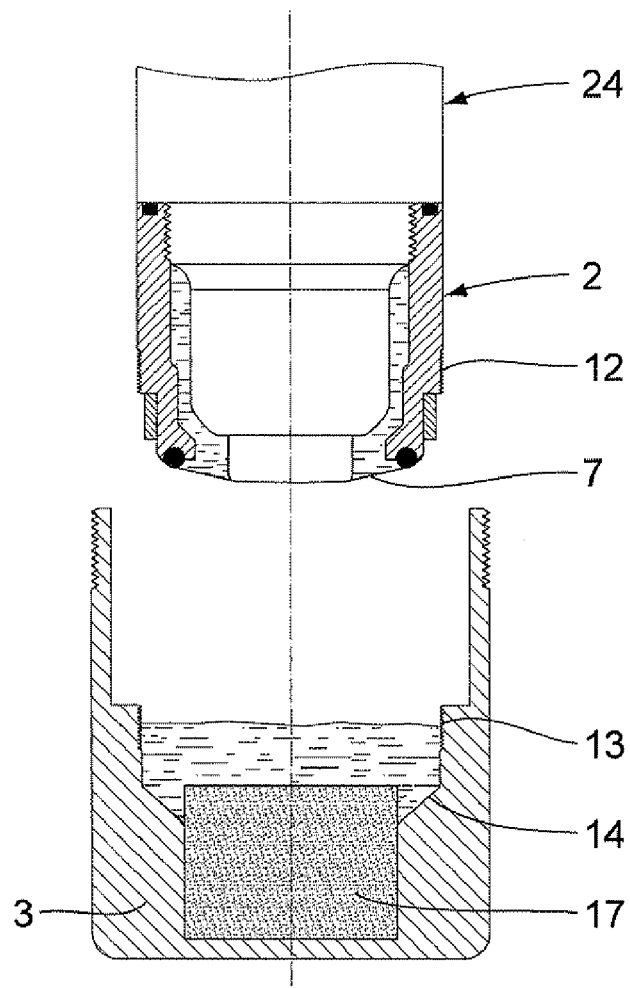

Since the pitch of threads 11 and 27 is reversed with respect to that of threads 12 and 13, an additional torque applied to sensor 24 in the direction of sensor 24 being screwed into cartridge 2, will provoke unscrewing of cartridge 2 from case 3 (see FIG. 5). This enables, on the one hand, to remove cartridge 2 from case 3 in a way that is easy and safe for the user and, on the other hand, to achieve a clamping torque of cartridge 2 on sensor 24, produced by the user, that is necessarily equal to a determined value, that is, to the clamping torque of cartridge 2 in case 3, which torque is produced by the manufacturer of the cartridge unit 1. A reliable fastening of cartridge 2 to sensor 24 may thus be guaranteed.

Figure 6:
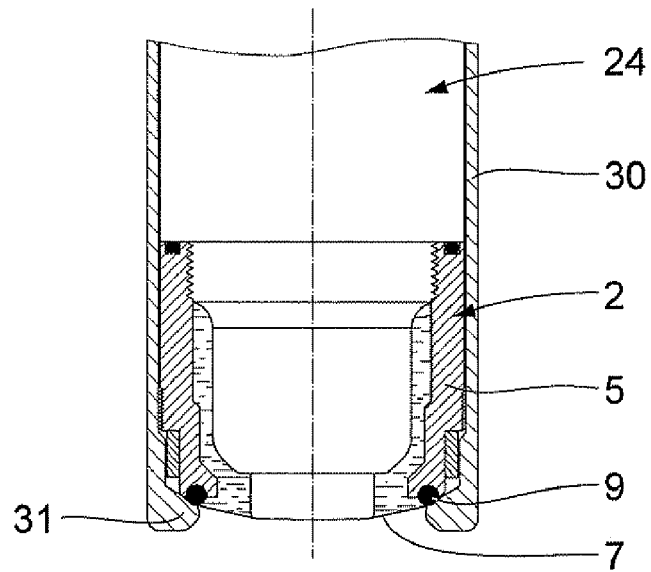

After the step illustrated in FIG. 5, case 3 containing the excess of electrolyte is discarded. Sensor 24, or at least cartridge 2, is introduced into a protecting sleeve 30, of metal for example, so that the material making up the cartridge body 5 and more generally all constitutive elements of cartridge 2 other than membrane 7 may be insulated from the sample to be analyzed (FIG. 6). Thus, sensor 24 does not have nooks where substances could accumulate and provoke the development of microorganisms. Sleeve 30 is fixed to sensor 24 by a clamping ring (not shown), for example. Sleeve 30 includes an inner annular ledge 31 that compresses gasket 9 in order to guarantee tightness of cartridge 2. Sensor 24 such as illustrated in FIG. 6 is ready for use. When desired, cartridge 2 can readily be detached from sensor 24, by removing the protecting sleeve 30 and then unscrewing cartridge 2, for instance with the aid of a tool identical or similar to case 3.

The invention claimed is:

1. Cartridge unit for an electrochemical sensor comprising:
   a cartridge prefilled with electrolyte comprising a first end closed by a selectively permeable membrane and having a first thread configured for fastening the cartridge to a supporting member, and a second end having a second thread configured for fastening the cartridge to the electrochemical sensor, wherein pitches of the first and second threads are reversed;
   said supporting member having a first cooperating thread arranged to be detachably fastened to the cartridge; and
   closing parts configured to fasten to said supporting member and cartridge to close the second end of the cartridge, said closing parts configured to be opened by a user,
   wherein the first cooperating thread of the supporting member is configured to cooperate with the first thread of the cartridge to receive a first clamping torque to fasten the cartridge to the supporting member, and a second cooperating thread of the electrochemical sensor is configured to cooperate with the second thread of the cartridge to receive a second clamping torque to fasten the cartridge to the electrochemical sensor, and
   further wherein the cartridge is configured so that the first thread of the cartridge detaches from the first cooperating thread of the supporting member when the second clamping torque is applied so that the cartridge is detachable from the supporting member.

2. Cartridge unit according to claim 1, wherein the supporting member comprises a case that entirely contains the cartridge.

3. Cartridge unit according to claim 2, wherein one of said closing parts comprises a lid for closing the case.

4. Cartridge unit according to claim 1, wherein the supporting member comprises a space intended to receive excess electrolyte from the cartridge during fastening of the cartridge to the electrochemical sensor.

5. Cartridge unit according to claim 1, wherein the first end of cartridge comprises a gasket retained by the membrane in a groove, this gasket being compressed by a surface of the supporting member.

6. Cartridge unit according to claim 1, wherein the second end of the cartridge comprises a gasket sitting in a groove and being compressed by the closing parts.

7. Cartridge unit according to claim 1, wherein the supporting member comprises an elastic member exerting pressure onto the outer surface of the membrane.

8. Cartridge unit according to claim 7, further comprising a member connected with the closing parts and resting against the inner surface of the membrane against the action of the elastic member in order to keep the membrane in a substantially undeformed state.

9. Assembly comprising a cartridge unit according to claim 1 and an electrochemical sensor.

10. Assembly according to claim 9, further comprising a protecting sleeve able to receive at least the cartridge after it has been fastened to the electrochemical sensor, this protecting sleeve protecting a body of the cartridge from a sample to be analyzed.

11. Assembly according to claim 10, wherein the first end of the cartridge comprises a gasket retained by the membrane in a groove, and wherein the protecting sleeve comprises a projecting member for compressing said gasket retained by the membrane in said groove.

* * * * *